United States Patent [19]
Korthoff et al.

[11] Patent Number: 5,474,732
[45] Date of Patent: Dec. 12, 1995

[54] FORMING LATCHLESS SURGICAL CLIP AND FIXTURE FOR USE THEREIN

[75] Inventors: Herbert W. Korthoff, Westport; Daniel Shichman, Trumbull; Ross R. Muth, Brookfield; Charles E. Gorman, Jr., Hamden, all of Conn.

[73] Assignee: United States Surgical Corporation, Norwalk, Conn.

[21] Appl. No.: 281,885

[22] Filed: Jul. 28, 1994

Related U.S. Application Data

[62] Division of Ser. No. 626,841, Dec. 13, 1990, Pat. No. 5,366,458.

[51] Int. Cl.⁶ .......................... B29C 61/06; B29C 59/18
[52] U.S. Cl. .......................... 264/230; 264/231; 264/235; 264/295; 264/339; 264/346; 425/188; 425/446
[58] Field of Search .................. 264/230, 231, 235, 264/295, 346, 339; 425/445–446, 188; 606/151

[56] References Cited

U.S. PATENT DOCUMENTS

| | | |
|---|---|---|
| 3,006,344 | 9/1961 | Vogelharger . |
| 3,091,828 | 6/1963 | Soltis . |
| 3,604,425 | 9/1971 | Leroy . |
| 3,757,629 | 9/1973 | Schneider . |
| 3,867,944 | 2/1975 | Samuels . |
| 4,274,415 | 6/1981 | Kanamoto et al. . |
| 4,317,451 | 3/1982 | Cerwin et al. . |
| 4,340,061 | 7/1982 | Kees, Jr. et al. . |
| 4,396,139 | 8/1983 | Hall et al. . |
| 4,418,694 | 12/1983 | Beroff et al. . |
| 4,476,865 | 10/1984 | Failla et al. . |
| 4,492,232 | 1/1985 | Green .................. 128/325 |
| 4,512,345 | 4/1985 | Green .................. 128/325 |
| 4,527,562 | 7/1985 | Mericle . |
| 4,612,932 | 9/1986 | Casper et al. . |
| 4,620,541 | 11/1986 | Gertzman et al. . |
| 4,638,804 | 1/1987 | Jewusiak . |
| 4,648,401 | 1/1987 | Mattson . |
| 4,741,337 | 5/1988 | Smith et al. . |
| 4,791,707 | 12/1988 | Tucker . |
| 4,796,627 | 1/1989 | Tucker . |
| 4,808,351 | 2/1989 | Mukherjee et al. .......... 264/235 |
| 4,821,721 | 4/1989 | Chin et al. . |
| 4,822,348 | 4/1989 | Casey . |
| 4,839,130 | 6/1989 | Kaplan et al. .......... 264/235 |
| 4,844,854 | 7/1989 | Kaplan et al. .......... 264/235 |
| 4,950,258 | 8/1990 | Kawai et al. .......... 604/281 |
| 4,957,500 | 9/1990 | Liang et al. . |
| 4,976,721 | 12/1990 | Blasnik et al. .......... 606/157 |
| 4,976,722 | 12/1990 | Failla . |
| 4,976,909 | 12/1990 | Dorband et al. .......... 264/235 |
| 4,983,176 | 1/1991 | Cushman et al. .......... 606/151 |
| 5,002,552 | 3/1991 | Casey .......... 606/157 |
| 5,026,379 | 6/1991 | Yoon .......... 606/141 |

FOREIGN PATENT DOCUMENTS

| | | |
|---|---|---|
| 0105414 | 9/1983 | European Pat. Off. . |
| 0326426 | 8/1989 | European Pat. Off. . |
| WO8300615 | of 1983 | WIPO . |
| WO9006089 | 6/1990 | WIPO . |

*Primary Examiner*—Jeffery R. Thurlow

[57] ABSTRACT

A method for forming a surgical clip and fixture for use therein includes molding a polymeric clip body, the clip body having hinged legs, the polymer of the clip body being substantially amorphous. The clip body can then be moved to a desired configuration while being subjected to a temperature above the glass transition temperature. The molded clip body is then heated to a temperature within the crystallization range for a period of time sufficient to impart at least 20% crystallinity thereto to impart a spring back property. Also disclosed herein is a fixture for forming a surgical clip in accordance with this method.

20 Claims, 6 Drawing Sheets

5,474,732

1

FORMING LATCHLESS SURGICAL CLIP AND FIXTURE FOR USE THEREIN

This is a divisional, of U.S. application Ser. No. 07/626,841 filed Dec. 13, 1990, now U.S. Pat. No. 5,366,458.

BACKGROUND OF THE INVENTION

The present invention relates to an improved polymeric surgical clip which on application provides a latchless, or non-locking, tissue clamping action.

Surgical clips are devices which are used to effect the occlusion and/or ligation of tissue, e.g., blood vessels, during surgery for such purposes as minimizing blood loss and maintaining the surgical site relatively free of blood.

A variety of surgical clip constructions and materials suitable for their manufacture are known. In addition to metals, surgical clips have been fabricated from a variety of non-bioabsorbable and bioabsorbable polymers, for example, those disclosed in U.S. Pat. Nos. 4,418,694; 4,476,865; 4,492,232; 4,512,345; 4,527,562; 4,557,263; 4,590,937; 4,620,541; 4,638,804; 4,646,741; and, 4,741,337. Specific non-bioabsorbable polymers which are known to be useful for the manufacture of surgical clips are polyesters, polyamides, polycarbonates, polyvinyl chloride, polysulfones, and polypropylenes. Bioabsorbable polymers which have been described as useful for forming surgical clips include homopolymers and copolymers of lactide, glycolide, caprolactone and p-dioxanone.

In known types of surgical clips, e.g., those described in the aforementioned prior U.S. patents, application of the clips to tissue results in a latching or locking of opposed clip elements, specifically, "leg" or "arm" members, which clamp the tissue in a vise-like grip. This grip, if excessive, could result in tissue damage and even necrosis. A further disadvantage of known latching clips is the possibility that the tissue or vessel to be clipped is over-sized such that, when applied, the clip is unable to latch or lock. In such applications, a likelihood exists that the clip will not effectively occlude or ligate the tissue as intended.

SUMMARY OF THE INVENTION

It is an object of the invention to provide a latchless surgical clip fabricated from a non-bioabsorbable or bioabsorbable polymer and capable of exerting only so much tissue clamping force as required to achieve effective hemostasis with little or no risk of damage to tissue.

It is another object of the invention to provide a latchless surgical clip possessing tissue clamping means on at least one opposed leg thereof, the tissue clamping means being uniquely configured to apply effective but non-excessive hemostasis.

It is a further object of the invention to provide a method for fabricating the aforesaid latchless surgical clips.

It is a specific object of the invention to provide a latchless surgical clip molded from a bioabsorbable polymer such as the aforementioned homopolymers and copolymers of lactide, glycolide, caprolactone, p-dioxanone, and the like.

In keeping with these and other objects of the invention, a latchless surgical clip is provided which comprises:

a polymeric clip body possessing a pair of legs, opposed surfaces of which constitute tissue clamping surfaces in the tissue clamping configuration of the applied clip, and a hinge possessing an elastic spring back property to which one end of each leg is attached, the other end

2 of each leg being free, each leg being movable about the hinge region; and latchless tissue clamping means on the tissue clamping surface of at least one leg, the tissue clamping means of the at least one leg cooperating with the opposed tissue clamping surface in the tissue clamping configuration of the clip to impart a tissue clamping force to the tissue.

Unlike the latching, or locking, surgical clips of the prior art, the latchless clip of the present invention provides a tissue clamping force which is self-adjusting for a variety of tissue types and tissue thicknesses. The ability of the latchless surgical clip to readily accommodate different tissue clamping situations with no appreciable risk of tissue injury represents a significant advantage over the latching, or locking, surgical clips of the prior art.

Also in keeping with the objects of the invention, a method for manufacturing a latchless surgical clip is provided which involves:

a) molding a polymeric clip body, the molded clip body comprising a pair of legs and a hinge region to which one end of each leg is joined, the molded clip body being substantially amorphous; and b) treating the molded clip body to impart at least 20% crystallinity thereto and to thereby impart a spring back property to the hinge region, the spring back property being sufficient to bias the legs toward a rest position from a deflected position.

DESCRIPTION OF THE PREFERRED EMBODIMENTS

Figure 1:
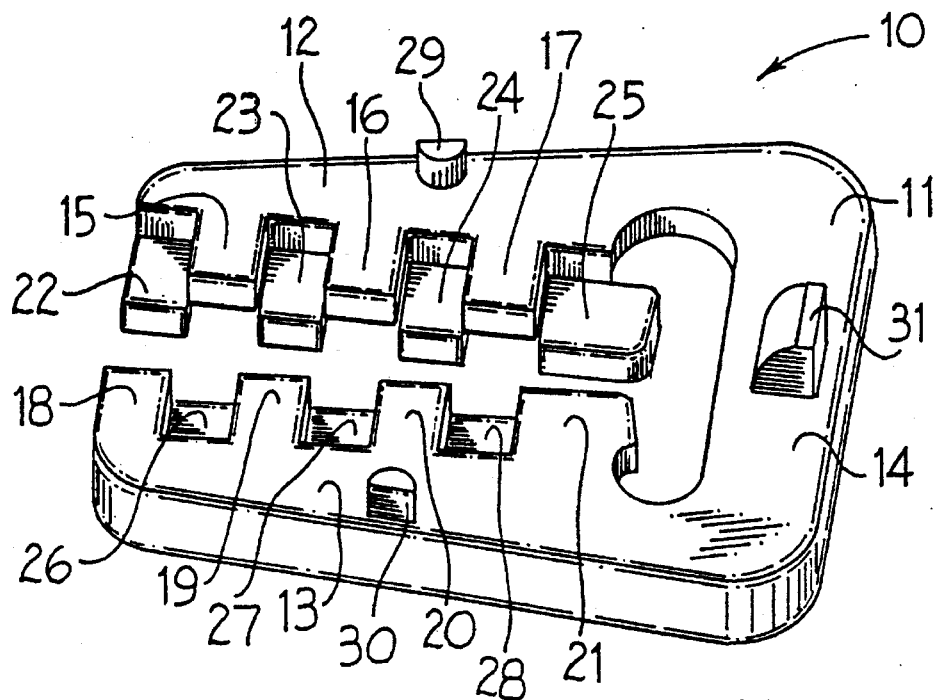
FIG. 1 is an enlarged perspective view of a latchless surgical clip of the present invention shown in the open, or pre-application, configuration, i.e., with its leg members spaced apart.

Referring to FIG. 1, latchless surgical clip 10 is provided as a single molded substantially planar polymeric clip body 11 possessing two legs 12 and 13 joined at one end through hinge region 14. Latchless surgical clip 10 is molded, e.g., by injection molding, in the open or pre-application configuration shown in FIG. 1, i.e., with leg 12 spaced away from leg 13. As molded, polymeric latchless clip 10 is substantially amorphous, i.e., the molded polymer exhibits less than 10% crystallinity. After molding in this open configuration, latchless clip 10 is treated so as to impart a spring-back property to hinge region 14.

A preferred post-molding clip treatment process involves heating latchless clip 10 to a temperature which permits legs 12, 13 to be moved or deflected into a second position which is different from the as-molded position. Inasmuch as molded clip 10 is substantially amorphous, clip 10 is typically heated to a temperature at or above the glass transition temperature of the polymeric material from which it is fabricated. Once at or above its glass transition temperature, the substantially amorphous polymer is soft or rubbery, thereby facilitating movement of legs 12, 13 to a second position.

Figure 2:
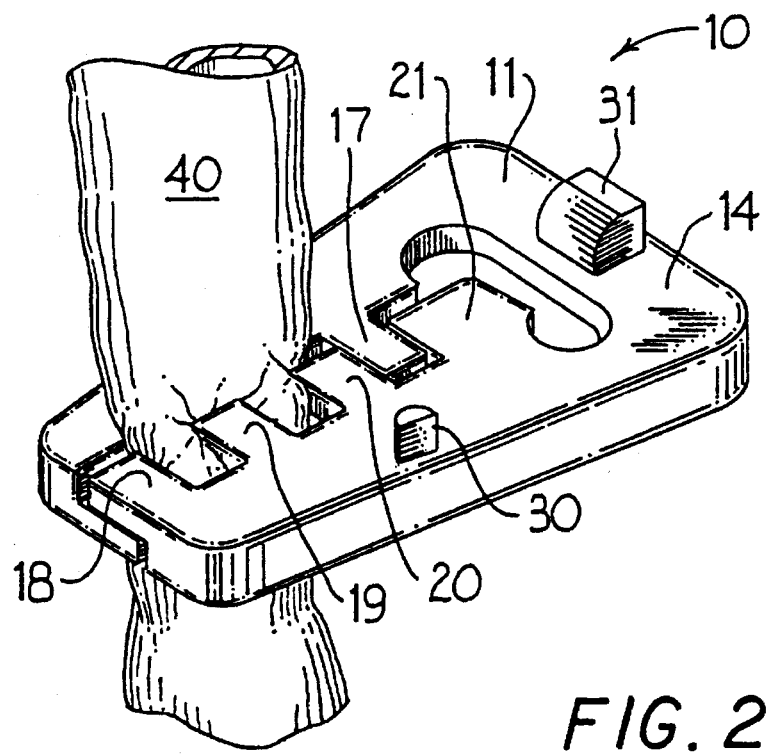
FIG. 2 is an enlarged perspective view of the latchless surgical clip of FIG. 1 in the closed, or tissue clamping, position as applied to vascular, e.g., arterial, tissue.

Typically legs 12, 13 are moved from a spaced position such as is shown in FIG. 1 to a position in which legs 12, 13 are closely aligned, e.g., the closed position shown in FIG. 2. However, it is also contemplated that legs 12, 13 might be moved to a second position in which legs 12, 13 are further spaced, e.g., a position approaching a 180° orientation. Surgical articles in which legs 12, 13 are moved to a further open position would not function as clips, but rather could serve to bias open tubular vessels or the like, as will be apparent to one of ordinary skill in the art.

Once deflected to this second position, clip 10 is further heated to a temperature at which crystallization of the polymer commences. In order to achieve the desired spring back property in hinge region 14, polymeric clip 10 is typically maintained at a crystallization temperature for a time sufficient to develop at least 20% crystallinity in clip 10, preferably at least 30% crystallinity, and most preferably at least 40% crystallinity.

The post-molding treatment of clip 10 typically results in a minor degree of shinkage of clip body 11. The post-molding treatment also typically causes a rounding of any sharp edges present on clip body 11. However, neither the shrinkage nor the rounding impinges upon the clinical efficacy of the device and, indeed, the rounding of sharp edges is generally desired to reduce the likelihood of tissue puncture or laceration upon clip application.

Figure 8:
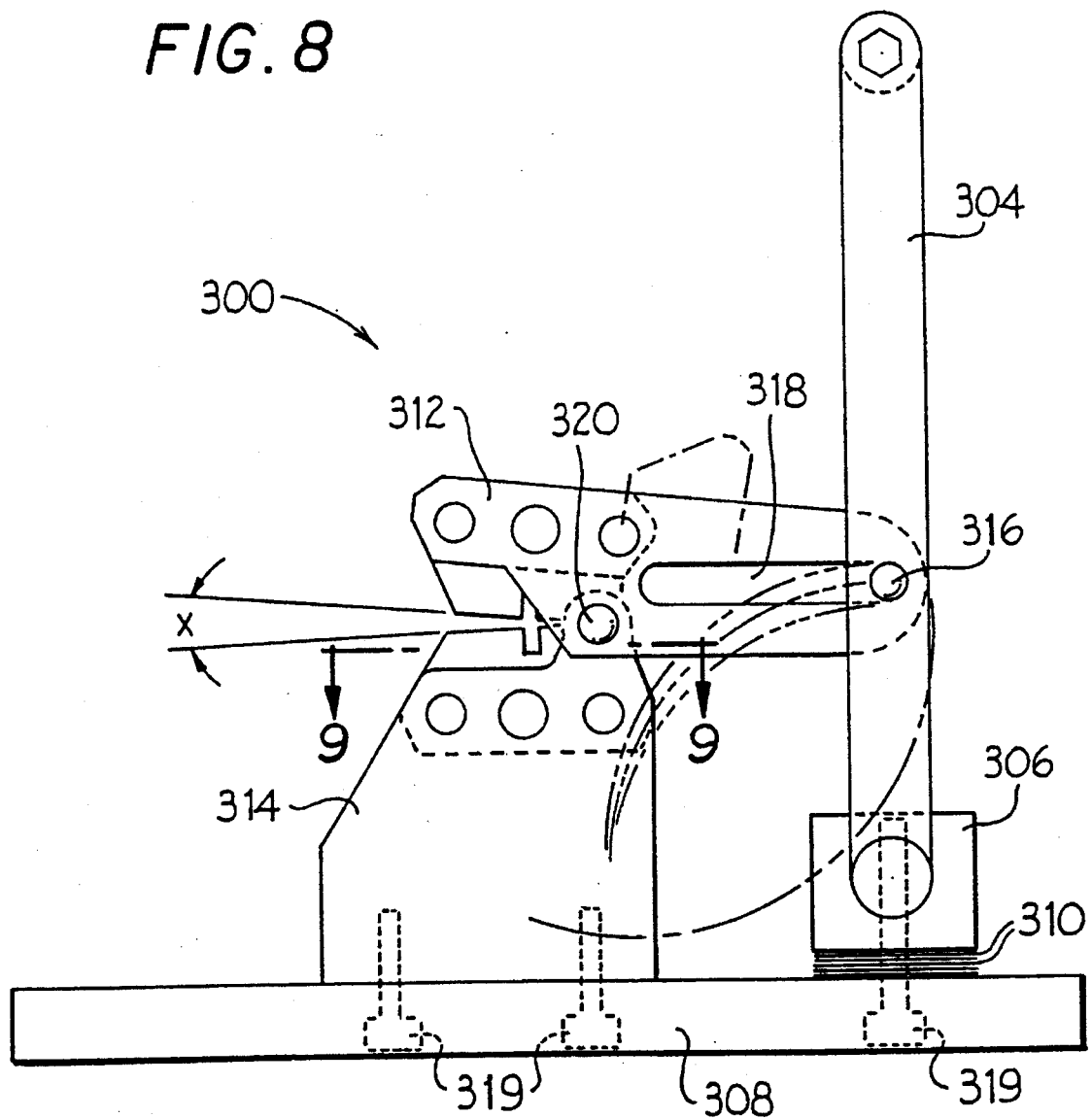
FIG. 8 is a side view, partially in section of a fixture for use in fabricating a latchless clip of the invention.
Figure 9:
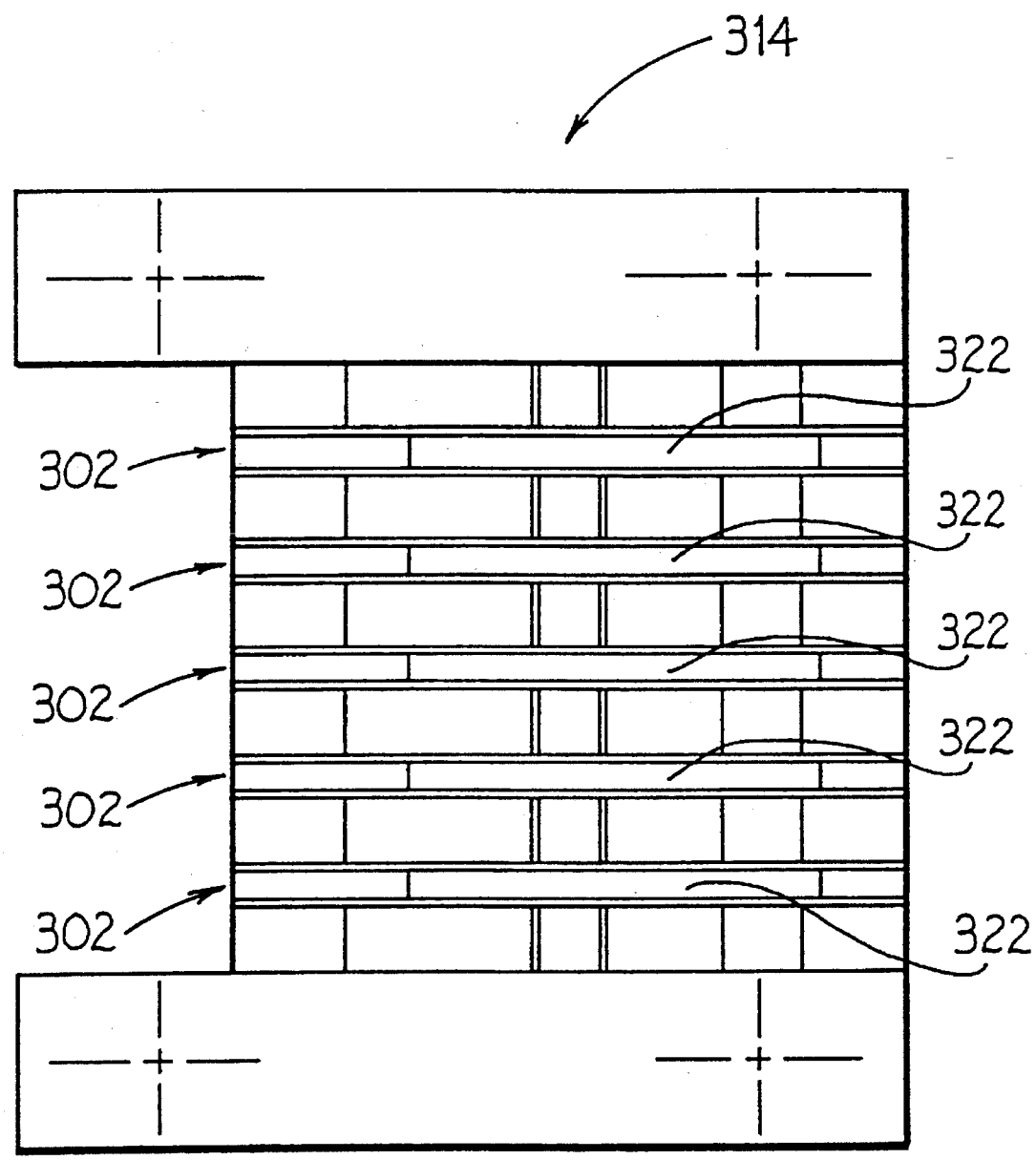
FIG. 9 is a top sectional view of the fixture of FIG. 8 taken along line 9—9.

During the crystallization of polymeric clip 10, it is important to maintain clip 10 in a substantially fixed position so as to impart the desired spring back property. A preferred method for moving clip 10 from the as-molded position to the aforesaid second position and for maintaining clip 10 in the second position during the crystallization step involves the utilization of a unique fixture. Referring to FIGS. 8 and 9, fixture 300 is adapted to apply a deflecting force to one or both of legs 12, 13 to move legs 12, 13 from the as-molded to the second position, and then to fix clip 10 in the second position during the crystallization step. Fixture 300 comprises a plurality of cavities 302, each being dimensioned to receive a molded latchless clip in an open position. Means for tightening the cavities to move the legs of the clip into a second position are also provided. In the pictured embodiment, fixture 300 includes tightening arm 304 which is pivotally mounted to block 306 on platform 308. Block 306 is adapted to cooperate with one or more shims 310. The number of shims 310 located below block 306 affects the angle x formed between pivotal arm 312 and stationary housing 314 of fixture 300 when in the second or closed position. Block 306 (with intermediate shims 310) and stationary housing 314 are mounted to platform 308 by bolts 319.

Tightening arm 304 possesses a transversely extending pin 316 which rides in linear slot 318 in pivotal arm 312. Pivotal arm 312 is mounted to stationary housing 314 at hinge pin 320. As shown in FIG. 9, the upper face of stationary housing 314 includes five channels 322 which define the lower halves of cavities 302. A corresponding series of channels (not pictured) is located in the lower face of pivotal arm 312.

To load fixture 300 with clips 10, tightening arm 304 is rotated counterclockwise from the position shown in FIG. 8 to a substantially horizontal orientation. Cooperation between pin 316 and slot 318 causes pivotal arm 312 to rotate clockwise to the substantially vertical position shown in phantom. Molded, substantially amorphous dips 10 are placed in channels 322 in stationary housing 314, with hinge region 14 positioned toward hinge pin 320. Tightening arm 304 may be maintained in its substantially vertical orientation or rotated clockwise such that the channels in pivotal arm 312 align with clips 10 to fully define cavities 302 before placing fixture 300 in an oven to heat clips 10.

After clips 10 are heated sufficiently to allow movement of legs 12, 13 to their second, or closed, configuration, fixture 300 is typically removed from the oven and tightening arm 304 is rotated clockwise to a substantially vertical position, as shown in FIG. 8. The angle x between pivotal arm 312 and stationary housing 314 when tightening arm 304 is vertical defines the spacing between legs 12, 13 in the closed position of clip 10. Cavities 302 are fixedly secured with legs 12, 13 in the second position through cooperation between tightening arm 304 and pivotal arm 312 when tightening arm 304 is in its vertical position. Fixture 300 is typically fabricated from a material providing effective and substantially uniform heat transfer to facilitate the heat treatment of clip 10, preferably stainless steel.

After sufficient crystallization is accomplished, clip 10 is cooled to ambient temperature and removed from fixture 300. Clip 10 remains oriented in its second position absent an external biasing force away from said second position, as discussed below. The above-described post-molding treatment impart an elastic spring back property to hinge region 14 such that when a biasing force is applied to legs 12, 13, e.g., a force biasing legs 12, 13 away from each other, and then withdrawn, legs 12, 13 spring back toward each other, i.e., to or toward their second (pre-spread) positions.

A wide variety of polymeric materials may be used to fabricate latchless clip 10 of the present invention. The principal requirement of the polymer is that it develop sufficient crystallinity upon movement to a second position to impart a sufficient spring back force to hinge region 14. Of course, the required spring back force will vary depending on the intended application of clip 10. Among the materials which are suitable for the manufacture of clip 10 are non-bioabsorbable polymers such as the polyesters, polyamides, polycarbonates, polyvinyl chloride, polysulfones, and polypropylenes. Suitable bioabsorbable polymers include homopolymers and copolymers of lactide, glycolide, trimethylene carbonate, caprolactone, and p-dioxanone, and blends thereof. A preferred bioabsorbable polymer is a copolymer derived from approximately 80 to 95 weight percent glycolide and 5 to 20 weight percent lactide.

In one preferred embodiment of the present invention, legs 12 and 13 each possess two parallel rows of spaced-apart staggered tooth-like projections, an upper row of projections 15, 16 and 17 on leg 12 cooperating with an upper row of projections 18, 19, 20 and 21 on leg 13, and a lower row of projections 22, 23, 24 and 25 on leg 12 cooperating with a lower row of projections 26, 27 and 28 on leg 13 to provide the closed, or tissue clamping, configuration of clip 10 shown in FIG. 2. That is, in the second or tissue clamping position, upper projections 15, 16, 17 of leg 12 are adapted to at least partially fit within the spaces formed between upper projections 18, 19, 20, 21 of leg 14 and to overlie lower projections 26, 27, 28. Similarly, projections 18, 19, 20, 21 are adapted to overlie lower projections 22, 23, 24 25 when clip 10 is in the second or tissue clamping position. Although the projections are shown to be substantially rectangular in shape, clearly projections of other configurations and sizes could be utilized. Additionally, a smaller or greater number of projections than are shown may be utilized to achieve the interfitting arrangement of the projections to enhance clip securement. It is also contemplated that spaced projections may be limited to the tissue clamping surface of one leg, these projections being adapted to cooperate with the tissue clamping surface of the opposing leg to effectively secure clip 10 to tissue.

Latchless clip 10 can be applied by any suitable device which possesses means for temporarily resiliently biasing legs 12 and 13 apart and placing the open clip into position at a desired tissue site. For example, clip 10 may be provided with upwardly extending pins 29, 30 and a forceps-like instrument can be utilized which grasps the closed clip in its jaws and, following engagement with pins 29 and 30, resiliently biases the legs apart the required amount to allow application of the clip to the desired tissue site, e.g., by directing a pushing force against the rear face of block 31 which brings the clip into engagement with blood vessel 40 as shown in FIG. 2. Once applied to the site, the biasing force is withdrawn whereupon legs 12 and 13 return to the closed, or tissue clamping, configuration thereby providing effective hemostasis.

Figure 3:
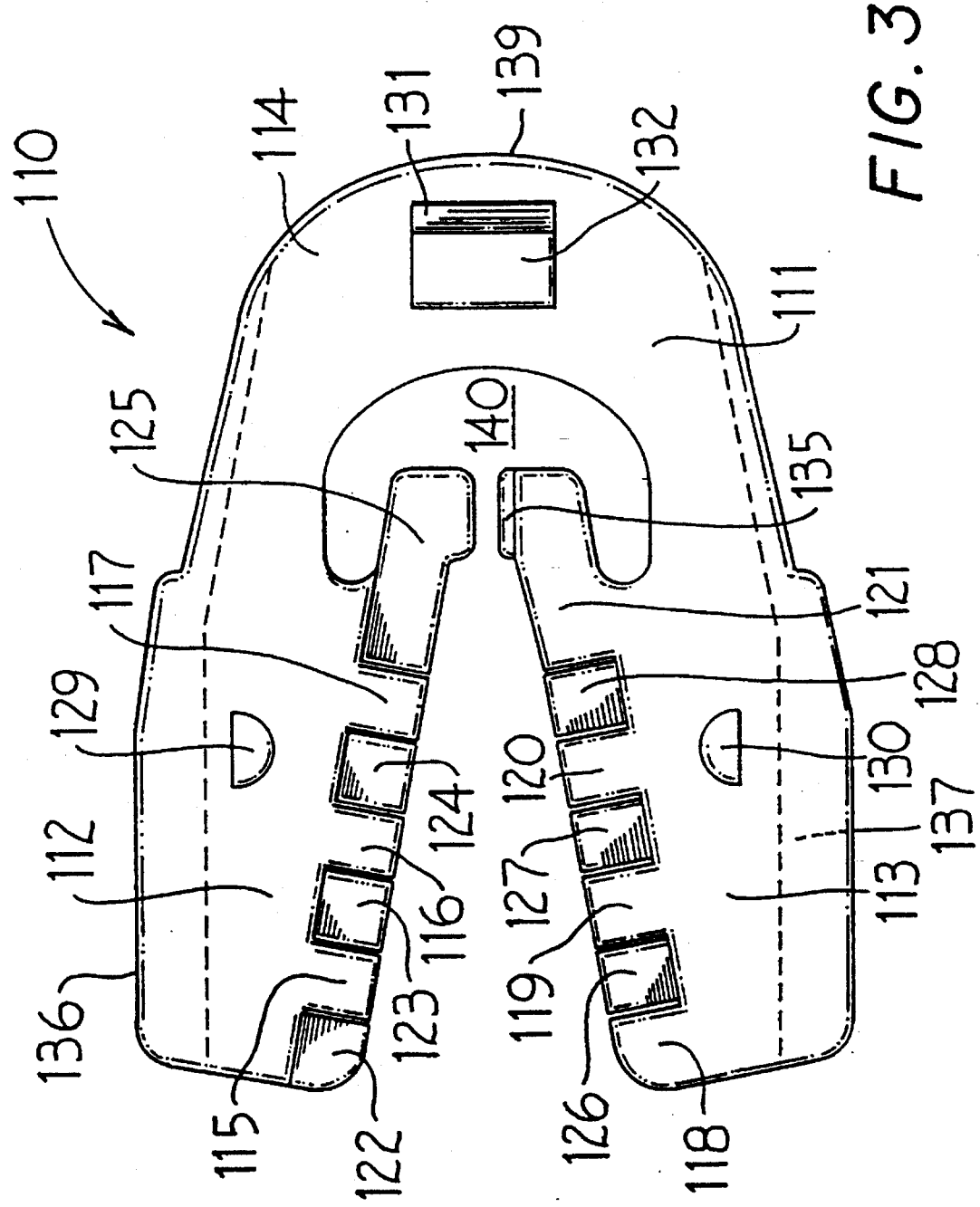
FIG. 3 is an enlarged perspective view of an alternate latchless surgical clip of the present invention shown in the open, or pre-application, configuration.
Figure 4:
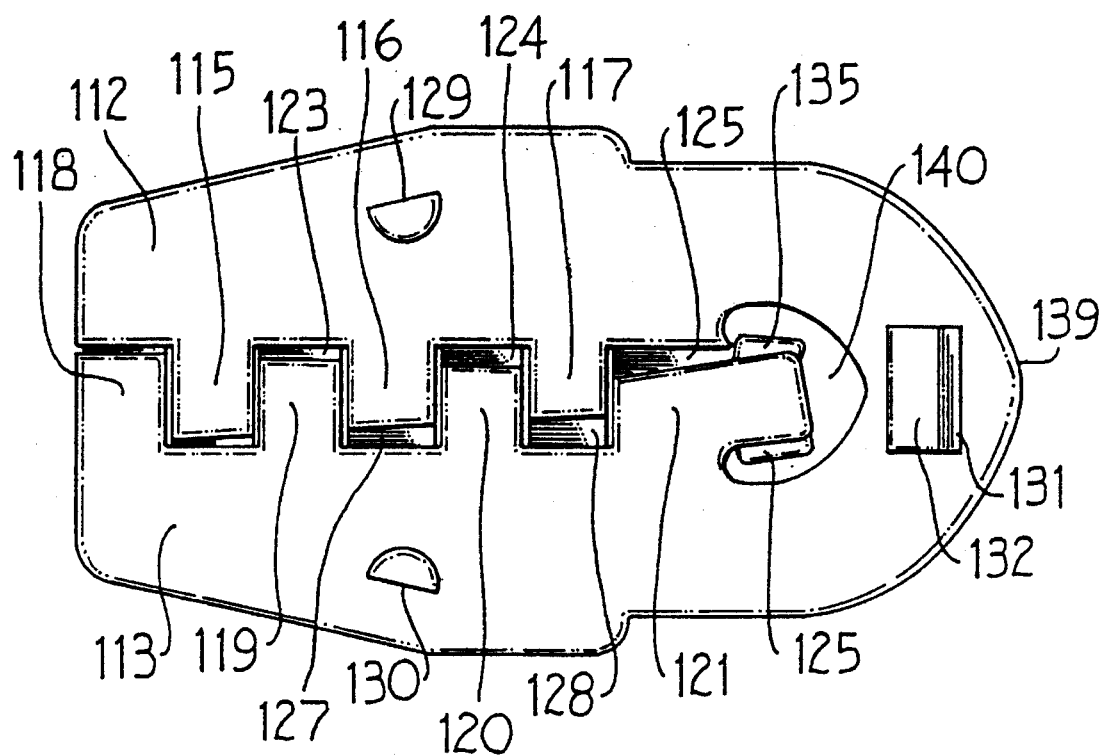
FIG. 4 is an enlarged perspective view of the latchless surgical clip of FIG. 3 in the closed, or tissue clamping, position.
Figure 5:
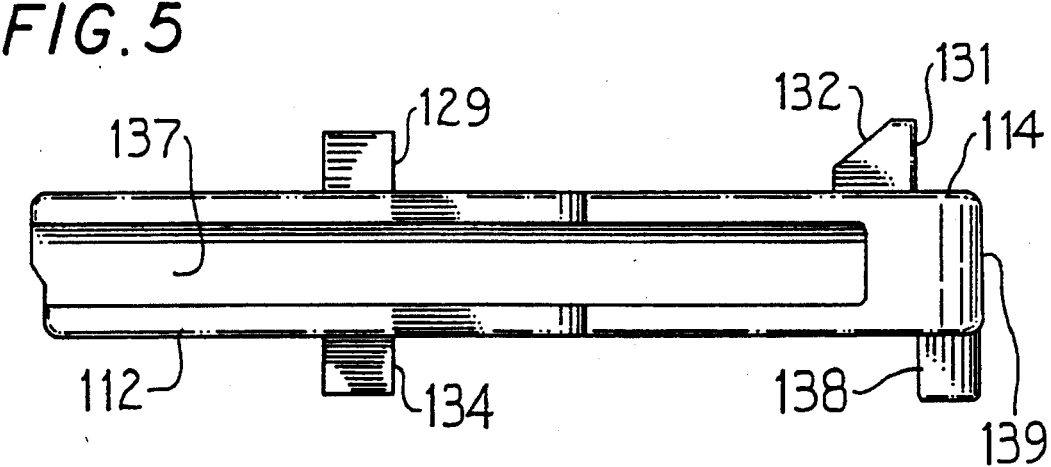
FIG. 5 is a side view of the latchless surgical clip of FIGS. 3 and 4.

An alternative latchless clip 110 of the present invention is shown in FIGS. 3-5. FIG. 3 illustrates the as-molded configuration of substantially planar latchless clip body 111 which includes legs 112, 113 each joined at one end to hinge region 114. Legs 112 and 113 each possess two parallel rows of spaced-apart staggered tooth-like projections, an upper row of projections 115, 116, 117 on leg 112 adapted to cooperate with an upper row of projections 118, 119, 120, 121 on leg 113. Projection 121 includes a lip 135 adapted to facilitate optimum cooperation with projection 125. A lower row of projections 122, 123, 124, 125 on leg 112 is adapted to cooperate with a lower row of projections 126, 127, 128 on leg 113. The cooperation between the staggered, toothlike projections on legs 112 and 113 in the second or tissue clamping position of clip 110 is illustrated in FIG. 4. Of course, depending on the size of the tissue to which clip 110 is applied, the degree to which the tooth-like projections on legs 112, 113 achieve the underlying and overlying positions shown in FIG. 4 will vary.

Referring additionally to FIG. 5, clip 110 includes upwardly extending pins 129, 130 and downwardly extending pins 133 (not pictured), 134 which extend from the upper and lower faces of legs 112, 113, respectively. As shown by the phantom lines in FIG. 3 and by the side view of FIG. 5, clip 110 also includes side channels 136, 137 which extend along the sides of legs 112, 113, respectively, and a portion of the sides of hinge region 114. Upwardly extending block 131 is centrally located on hinge region 114 and includes a cam surface 132. Hinge region 114 also includes downwardly extending post 138 substantially aligned with rear face 139 of hinge region 114.

Clip 110 may be applied to tissue using a suitable device which possesses means for temporarily biasing legs 112, 113 apart and for placing the open clip into position at a desired tissue site. Upwardly and downwardly extending pins 129, 130, 133, 134 provide interacting means which facilitate temporarily biasing legs 112, 113 apart by the biasing means of the application device. Inclusion of interacting means extending both upwardly and downwardly relative to clip body 111 helps to minimize the possibility that clip 110 may torque, bow or rotate as the application device temporarily biases legs 112, 113 apart. Similarly, channels 136, 137 provide guide and alignment means to clip 110 which facilitate cooperation of clip body 111 with the clip placement means, e.g., forceps jaws, throughout the clip placement process. Upwardly extending block 131 allows clip 110 to be positioned in the desired location for clip placement, e.g., through application of a pushing force on the rear face of block 131. Cam surface 132 facilitates positioning of a pushing means behind block 131 from an initial position forward of block 131, e.g., adjacent gap region 140 forward of hinge region 114. Downwardly extending pin 138 is useful as an indexing means for clip 110 as it is positioned for placement on or around tissue.

Figure 6:
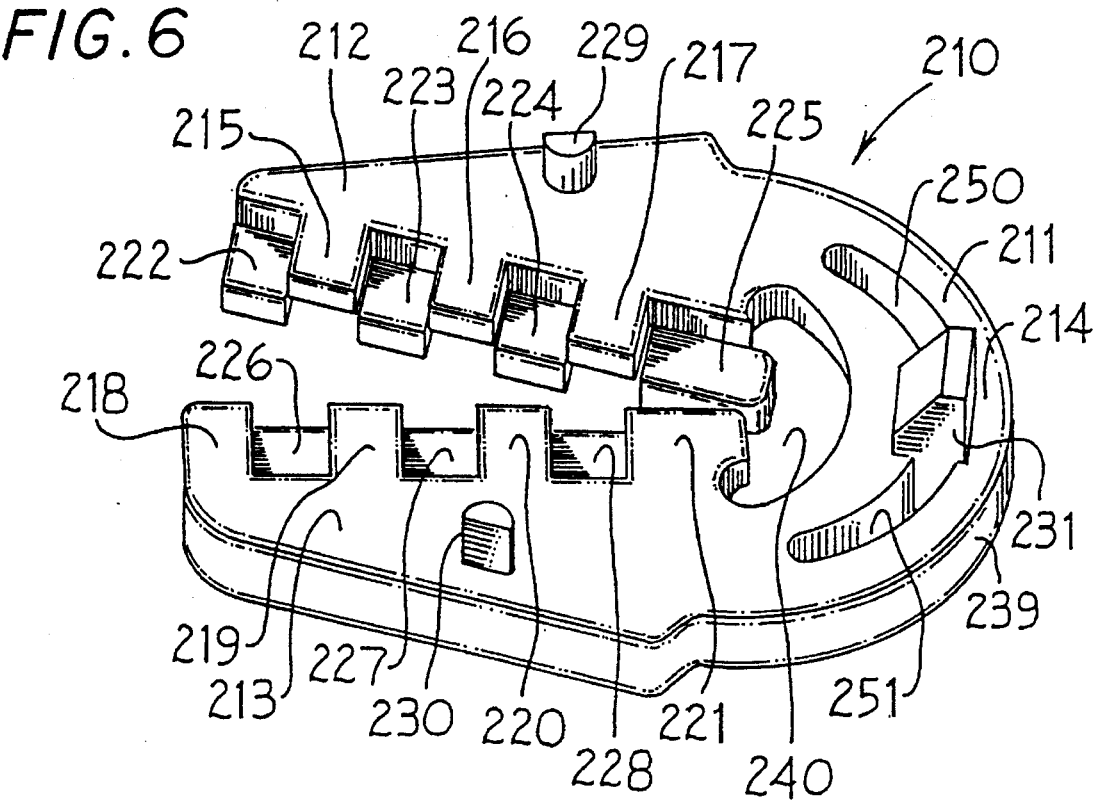
FIG. 6 is an enlarged perspective view of a further alternate latchless surgical clip of the present invention shown in the open, or pre-application configuration.
Figure 7:
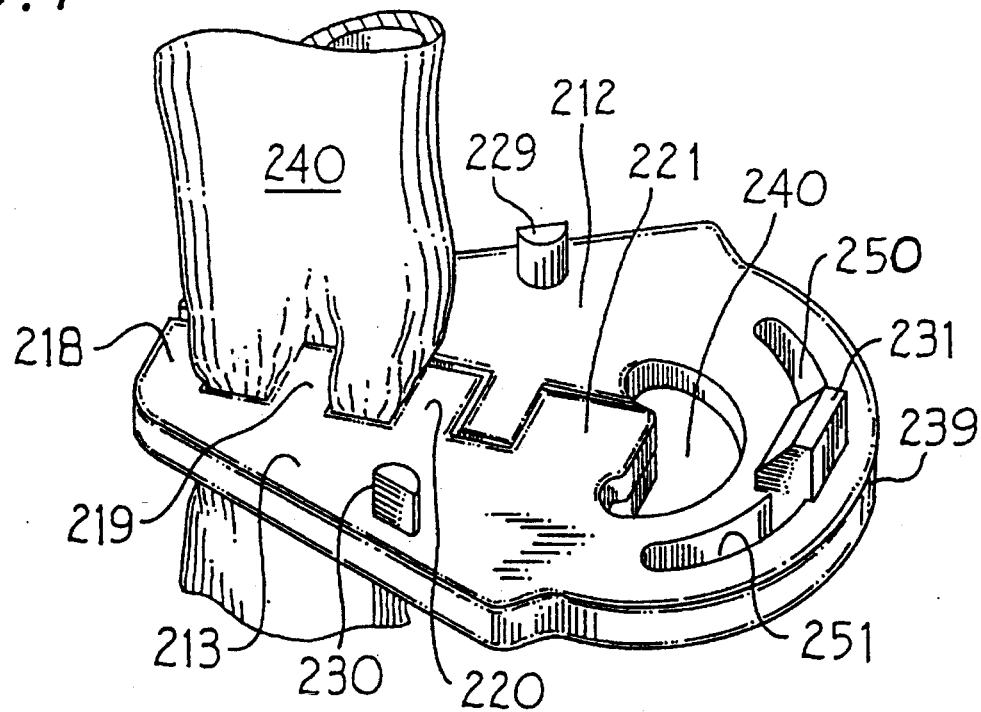
FIG. 7 is an enlarged perspective view of the latchless surgical clip of FIG. 6 in the closed, or tissue clamping, position.

A second alternative surgical clip 210 of the present invention is shown in FIGS. 6 and 7. As with the clip embodiments described hereinabove, substantially planar clip body 211 includes legs 212, 213 each connected at one end to hinge region 214. Legs 212, 213 have tooth-like projections (215 to 228) which cooperate in the closed or tissue clamping position of FIG. 7 to apply a tissue clamping force to tissue 40.

Clip 210 differs from the earlier embodiments in that wedge-shaped cored out sections 250, 251 flank block 231 in hinge region 214. Cored out sections 250, 251 provide an enhanced distribution of the stress forces which occur in clip 210 during its flexure, the majority of stress forces being experienced in the area in which legs 212, 213 are joined to hinge region 214, particularly when legs 212 and 213 of clip 210 are biased into the open configuration. Cored out sections 250, 251 are preferably located closer to back face 239 of hinge region 214 than gap region 240. Although not desiring to be limited to one theory, it is believed that cored out sections 250, 251 serve to move the centroids of respective sides of clip body 211 toward their respective centers, placing the greater percentage of forces experienced by clip body 211 during outward deflection of legs 212, 213 in compression, as opposed to in tension. Cored out sections 250, 251 thus improve the mechanical integrity and functional reliability of clip 210. Cored out sections 250, 251 also facilitate even heating and cooling of clip body 211 upon molding and throughout the post-molding treatment experienced by dip 210.

The specific geometry and sizes of the cored sections can vary based on the design of the clip, the likely flexural forces to which it will be exposed, and the polymer from which it is fabricated. The cored sections may extend completely through the hinge region 214, i.e., to form an aperture therethrough, or may constitute a scallop or slot in the upper, the lower or in both faces of hinge region 214. In a preferred embodiment of the cored clip 210 of the invention, cored out sections 250, 251 are slots formed in the upper face of hinge region 214, the slots extending to a depth of about 30 to 75% of the thickness of hinge region 214. In these slotted embodiments, the web regions which exist at the base of slotted cored out sections 250, 251, i.e., on the bottom face of hinge region 214, impart additional integrity to clip body 211.

The flexural strength of the latchless clip of the invention may also be increased through a post-flexing process after the clip has been subject to a post-molding treatment to achieve the desired degree of crystallinity and of spring back property in the hinge region. Post-flexing involves repeatedly and temporarily biasing the legs apart through application of a temporary biasing force at an elevated temperature, e.g., 30°–50° C. Such post-flexing treatment has been found to lessen the internal stresses experienced by the clip when being applied to tissue at ambient temperature.

The clip of the present invention may be constructed in various sizes according to their intended function. For example, for a latchless clip to be used in hemostatically occluding a blood vessel, a length of about 1 cm, a width of about 5 mms and vessel clamping surfaces of about 5 mms in length are typical. The dimensions may be reduced as appropriate, e.g., by about 50% for microsurgical applications. Conversely, the dimensions may be increased as appropriate, e.g., by about 100% for female sterilizations in which oviduct occlusion is desired. For male sterilizations, occlusion of the vas deferens may be accomplished with smaller clips. The clip can be molded in various colors to increase color contrast with surrounding tissue and/or to facilitate identification of the size of the clip.

The clip body, particularly the hinge region and legs, of the latchless surgical clip of the invention possesses sufficient resilience to permit the clip legs to be deflected apart an appropriate distance to allow the clip to be easily and efficiently placed on or around the desired tissue. Generally, the clip body is sufficiently resilient to permit the legs to be deflected to a position wherein the legs are separated by an angle of from 15° to 50°, and more typically an angle of from 20° to 35°. This angle of maximum deflection will depend on such factors as the polymeric material, the degree of crystallinity of the clip body after the post-molding treatment, the physical dimensions of the clip body, the presence of cored sections, and whether the clip body has experienced post-flexing. The angle of maximum deflection may correspond to, but is not necessarily restricted to, the angular opening of the legs in the as-molded configuration.

The hinge region also possesses a sufficient spring back force to bring the legs toward each other (once the external biasing force is removed from the legs) to apply an effective tissue clamping force to the tissue. The tissue clamping force which the clip must deliver will depend on such factors as the type and size of the tissue to which it is to be applied. Typically, in order for the clip to effectively occlude a tissue structure, e.g., a blood vessel, the clip should apply a residual force of about 0.5–1.0 psi once placed on the tissue structure. Once placed on tissue, a hemostatic latchless clip must maintain that position for a period of time sufficient to permit hemostasis to take place, i.e., maintain its strength in vivo so as to withstand the internal pressure which is trying to force the tissue structure back open until the natural, permanent sealing of the tissue structure is complete.

EXAMPLE

A latchless surgical clip mold having a cavity configuration substantially corresponding to the clip design shown in FIG. 3 was charged with a molten copolymer (90% glycolide/10% lactide) which entered at a temperature of 220° to 230° C. The mold had an initial temperature of about 20° C. The mold was quickly cooled to ambient temperature to form a substantially amorphous (less than 10% crystallinity) latchless clip having legs in an open position, defining an angle of about 25°. After a few seconds, the clip was removed from the mold cavity and placed in a stainless steel post-molding treatment fixture of the type shown in FIGS. 8 and 9.

The clip-containing fixture was heated to raise the polymeric clip to a temperature above the glass-transition temperature of the polymer, i.e., to a temperature of about 40° C., for about four minutes. The fixture was then tightened so as to bring the legs into a substantially parallel, interfitting relationship (see FIG. 4). Once in the substantially parallel position, the fixture was fixedly secured and the temperature was increased to within the crystallization temperature range of the polymeric clip, i.e., to a temperature of about 85° C. The clip was maintained in this position and within this temperature range for about two hours. (The crystallization of the subject polymer is exothermic; heat was removed from the system as appropriate to maintain the desired temperature range.) The fixture was then cooled and the latchless clip which possessed approximately 40–45% crystallinity was removed therefrom.

The thus treated latchless surgical clip exhibited significant resilience in that the clip legs could be repeatedly deflected to an angular opening of about 25° to 30° and released without cracking, fatigue or failure of the clip body. The hinge region exhibited an effective spring back property in that each time the biasing force required to deflect the legs to the open position was removed, the legs were immediately and automatically drawn back together. The tissue clamping surfaces of the legs imparted an effective tissue clamping force to a tissue structure, without the presence of a latching or locking mechanism.

Having now described the present invention and certain specific embodiments thereof, it will be readily apparent to one skilled in the art that many variations and modifications may be made to the present invention without departing from the spirit and scope thereof.

What is claimed is:

1. A method for forming a latchless surgical clip comprising:

a) molding a polymeric clip body, said molded clip body comprising a pair of legs and a hinge region to which one end of each leg is joined, said molded clip body being substantially amorphous; and b) treating said molded clip body at a temperature within the crystallization range, wherein said legs are in a predetermined rest position, said treating at said temperature within the crystallization range being maintained for a period of time sufficient to impart at least 20% crystallinity thereto to impart a spring back property to said hinge region, said spring back property being sufficient to bias said legs toward said rest position in response to deflection of said legs from said rest position to a deflected position.

2. The method of claim 1 wherein said pair of legs are molded in an open, spaced apart position.

3. The method of claim 2 further comprising moving said legs from said open, spaced apart position to a substantially parallel, aligned position.

4. The method of claim 3 wherein said legs are moved at a temperature above the glass transition temperature of said polymeric body.

5. The method of claim 1 further comprising post-flexing said treated clip body to lessen stresses therein.

6. A fixture for forming a latchless surgical clip comprising:

a cavity sized and dimensioned to receive a molded latchless clip, said latchless clip comprising a pair of legs and a hinge region to which one end of each leg is joined, said legs being in an open, spaced apart position;

means for tightening the cavity to move said legs into a second position different from said open, spaced apart position; and means for fixedly securing said cavity with said legs in said second position.

7. The fixture of claim 6 further comprising a support frame which includes a base, and a stationary housing attached to said base for supporting said cavity.

8. The fixture of claim 7 wherein said means for tightening the cavity comprises a tightening arm having an end which is pivotally attached to said support frame.

9. The fixture of claim 8 wherein said means for fixedly securing said cavity comprises a pivotal arm which is pivotally attached to said stationary housing and being movable between open and closed positions in response to movement of said tightening arm.

10. The fixture of claim 9 wherein said tightening arm includes a transversely extending pin which extends through an elongated slot in the pivotal arm, said tightening arm being movable between a substantially vertical first position in which said pivotal arm is in the closed position and a second position wherein said pivotal arm is in the open position.

11. The fixture of claim 10 wherein said cavity is defined by a channel in each of the stationary housing and the pivotal arm.

12. A method for forming a surgical clip comprising:

a) molding a polymeric clip body, said molded clip body comprising a pair of legs joined at a hinge region, said molded clip body being substantially amorphous, and said clip body being molded in a first configuration wherein said legs are in a first position;

b) moving said clip body from said first configuration to a second configuration wherein said pair of legs are in a second position, and, c) heating said molded clip body to a temperature within the crystallization range for a period of time sufficient to impart at least 20% crystallinity thereto to impart a spring back property to said hinge region, said spring back property being sufficient to bias said legs toward said second position in response to deflection of said legs from the second position.

13. The method of claim 12 wherein said first position of the legs is an open, spaced apart position.

14. The method of claim 13 wherein said second position of said legs is a closed position wherein said legs are substantially parallel.

15. The method of claim 12 wherein the step of moving said clip body from the first configuration to the second configuration is performed while subjecting the clip body to a temperature above the polymeric glass transition temperature.

16. The method of claim 12 wherein said temperature within the crystallization range is at least about 85° C.

17. The method of claim 12 wherein heat is removed from the clip body to maintain said temperature within the crystallization range.

18. The method of claim 12 wherein at least about 30% crystallization imparted to the surgical clip.

19. The method of claim 12 wherein at least about 40% crystallinity is imparted to the surgical clip.

20. The method of claim 12 wherein the polymeric clip body is fabricated from a copolymer of 90% glycolide/10% lactide.

* * * * *